United States Patent [19]
Bousseau et al.

[11] Patent Number: 5,629,312
[45] Date of Patent: May 13, 1997

[54] USE OF LAMOTRIGINE FOR TREATING AIDS-RELATED NEURAL DISORDERS

[75] Inventors: Anne Bousseau; Adam Doble; Erik Louvel, all of Paris, France

[73] Assignee: Rhone-Poulenc Rorer S.A., Antony, France

[21] Appl. No.: 530,253

[22] PCT Filed: Feb. 25, 1994

[86] PCT No.: PCT/FR94/00210

§ 371 Date: Sep. 1, 1995

§ 102(e) Date: Sep. 1, 1995

[87] PCT Pub. No.: WO94/20108

PCT Pub. Date: Sep. 15, 1994

[30] Foreign Application Priority Data

Mar. 5, 1993 [FR] France .................................. 93 02568

[51] Int. Cl.$^6$ .................................................. A61K 31/53
[52] U.S. Cl. ........................................................ 514/242
[58] Field of Search .............................................. 514/242

[56] References Cited

FOREIGN PATENT DOCUMENTS

0247892A1  12/1987  European Pat. Off. .

OTHER PUBLICATIONS

Sussman et al., "Dramatic Response to Lamotrigine in Two Patients With Neurologic Deficits Secondary to Frequent Intractable Seizures", Epilepsia, 30(5):662 (1989).

Nakamura–Craig et al., "Analgesic Effects of Lamotrigine in an Experimental Model of Neuropathic Pain in Rats", British Journal of Pharmacology, 107, p. 336P (1992).

Koppel et al., "Antiepileptic Drug Treatment in Patients With Aids", Epilepsia, 33(3):69 (1992).

Meldrum et al., "Excitatory Amino Acid Receptors And Disease", Current Opinion in Neurology and Neurosurgery, 5(4):508–513 (1992).

Kieburtz et al., "Excitotoxcity And Dopaminergic Dysfunction in The Acquired Immunideficiency Syndrome Dementia Complex", Arch. Neurol. 48(12):1281–1284 (1991).

Primary Examiner—Raymond Henley, III
Attorney, Agent, or Firm—Finnegan, Henderson, Farabow, Garrett & Dunner, L.L.P.

[57] ABSTRACT

The use of lamotrigine or pharmaceutically acceptable salts thereof for treating AIDS-related neuronal disorders is disclosed.

4 Claims, No Drawings

USE OF LAMOTRIGINE FOR TREATING AIDS-RELATED NEURAL DISORDERS

The present invention relates to a novel therapeutic application of lamotrigine or the pharmaceutically acceptable salts of this compound.

Lamotrigine or the pharmaceutically acceptable salts of this compound are described as anticonvulsants and antiepileptics, in particular in Patent EP 247,892.

It has now been found, surprisingly, that this compound may also be used in the treatment of neuro-AIDS.

The term neuro-AIDS includes disorders involving dementia, cognitive disorders, neuropathies, myopathies, ocular disorders and all neurological symptoms associated with the HIV-1 virus.

The activity of lamotrigine in neuro-AIDS was demonstrated in the test of neuronal death induced by the GP-120 protein, an envelope protein of the HIV-1 virus, according to the following protocol:

Cortical cell cultures are prepared according to the method described by SINDOU et al., Brain Res., 572, 242–246 (1992). After 8 to 10 days of culture, neurons which have acquired a correct neuritic shape are used for the tests. The cells are kept at 37° C. in a $CO_2$ incubator for the whole of the experiment.

Neuronal survival is assessed before application and after 24 hours of application of the test product by a colorimetric technique using Tuspan Blue, counting predetermined fields (semi-quantitative method). A minimum of 4 culture dishes per concentration (100 neurons per dish) were analysed.

In a first series, neuronal survival of the culture medium was determined without any product. Neuronal survival is then approximately 87%.

In a second series, the toxicity of the GP120 in culture was demonstrated. The GP120 was applied alone to the culture medium for 24 hours at a concentration of 20 pmol, and brings about a neuronal death which is of the order of 43%.

In the third series, the test product dissolved in dimethyl sulphoxide ($10^{-3}$M) is applied 5 minutes before the application of GP120 and thereafter incubated for 24 hours at concentrations from $10^{-7}$ to $10^{-8}$ mol. Neuronal survival is greater than 80%.

As pharmaceutically acceptable salts, there may be mentioned, in particular, the addition salts with inorganic acids, such as hydrochloride, sulphate, nitrate or phosphate, or organic acids, such as acetate, propionate, succinate, oxalate, benzoate, fumarate, maleate, methanesulphonate, isethionate, theophyllineacetate, salicylate, phenolphthalinate, methylenebis($\beta$-hydroxynaphthoate) or substitution derivatives of these derivatives.

The medicinal products consist at least of lamotrigine, in free form or in the form of an addition salt with a pharmaceutically acceptable acid, in the pure state or in the form of a composition in which it is combined with any other pharmaceutically compatible product, which may be inert or physiologically active. The medicinal products according to the invention may be employed orally or parenterally.

As solid compositions for oral administration, tablets, pills, powders (gelatin capsules, wafer capsules) or granules may be used. In these compositions, the active principle according to the invention is mixed with one or more inert diluents such as starch, cellulose, sucrose, lactose or silica, under a stream of argon. These compositions can also comprise substances other than diluents, for example one or more lubricants such as magnesium stearate or talc, a colorant, a coating (dragées) or a varnish.

As liquid compositions for oral administration, pharmaceutically acceptable solutions, suspensions, emulsions, syrups and elixirs, containing inert diluents such as water, ethanol, glycerol, vegetable oils or liquid paraffin, may be used. These compositions can comprise substances other than diluents, for example wetting, sweetening, thickening, flavouring or stabilizing products.

The sterile compositions for parenteral administration can preferably be suspensions, emulsions or aqueous or non-aqueous solutions. As a solvent or vehicle, water, propylene glycol, a polyethylene glycol, vegetable oils, especially olive oil, injectable organic esters, for example ethyl oleate, or other suitable organic solvents may be employed. These compositions can also contain adjuvants, especially wetting agents, tonicity agents, emulsifiers, dispersants and stabilizing agents. The sterilization may be carried out in several ways, for example by. aseptic filtration, by incorporating sterilizing agents in the composition, by irradiation or by heating. They may also be prepared in the form of sterile solid compositions which can be dissolved at the time of use in sterile water or any other sterile injectable medium.

The doses depend on the effect sought, the treatment period and the administration route used; they are generally between 50 and 400 mg per day orally for an adult, with single doses ranging from 25 to 200 mg of active substance.

Generally speaking, the doctor will determine the appropriate dosage in accordance with the age and weight and all other factors distinctive to the subject who is to be treated.

The examples which follow illustrate some medicinal products according to the invention:

EXAMPLE A

Tablets containing a 50 mg dose of active product and having the following composition are prepared according to the usual technique:

| | |
|---|---|
| Active product | 50 mg |
| Mannitol | 64 mg |
| Microcrystalline cellulose | 50 mg |
| Povidone excipient | 12 mg |
| Carboxymethylstarch sodium | 16 mg |
| Talc | 4 mg |
| Magnesium stearate | 2 mg |
| Colloidal silica, anhydrous | 2 mg |

Mixture of methylhydroxypropylcellulose, polyethylene glycol 6000 and titanium dioxide (72:3.5:24.5)

q.s. 1 finished film-coated tablet weighing 245 mg

EXAMPLE B

Hard gelatin capsules containing a 50 mg dose of active product and having the following composition are prepared according to the usual technique:

| | |
|---|---|
| Active product | 50 mg |
| Cellulose | 18 mg |
| Lactose | 55 mg |
| Colloidal silica | 1 mg |
| Carboxymethylstarch sodium | 10 mg |
| Talc | 10 mg |
| Magnesium stearate | 1 mg |

EXAMPLE C

An injectable solution containing 10 mg of active product and having the following composition is prepared:

| | |
|---|---|
| Active product | 10 mg |
| Benzoic acid | 80 mg |
| Benzyl alcohol | 0.06 cm$^3$ |
| Sodium benzoate | 80 mg |
| Ethanol, 95% | 0.4 cm$^3$ |
| Sodium hydroxide | 24 mg |
| Propylene glycol | 1.6 cm$^3$ |
| Water q.s. | 4 cm$^3$ |

The invention also relates to the process for preparing medicinal products which are useful in the treatment of neuro-AIDS, consisting in mixing lamotrigine or the pharmaceutically acceptable salts of this compound with one or more compatible and pharmaceutically acceptable diluents and/or adjuvants.

We claim:

1. A method for increasing neuronal survival in the presence of GP-120 protein in a host infected with the HIV-1 virus, comprising administering to a host in need thereof an effective amount of lamotrigine or a pharmaceutically acceptable salt thereof.

2. A method according to claim 1, further comprising treating dementia, cognitive disorders, neuropathies, myopathy, and ocular disorders associated with the presence of said GP-120 protein through the administration of an effective amount of lamotrigine or its pharmaceutically acceptable salt.

3. A method for reducing neuronal death induced by the GP-120 protein in a host infected with the HIV-1 virus, comprising administering to a host in need thereof an effective amount of lamotrigine or a pharmaceutically acceptable salt thereof.

4. A method according to claim 3, further comprising treating dementia, cognitive disorders, neuropathies, myopathy, and ocular disorders associated with the presence of said GP-120 protein through the administration of an effective amount of lamotrigine or its pharmaceutically acceptable salt.

* * * * *